US009775492B2

(12) United States Patent
Saito

(10) Patent No.: US 9,775,492 B2
(45) Date of Patent: Oct. 3, 2017

(54) IMAGE DEVICE FOR SYNCHRONIZING TIMING OF IMAGING BY FIRST AND SECOND IMAGE SENSORS, AND ENDOSCOPIC DEVICE

(71) Applicant: OLYMPUS CORPORATION, Tokyo (JP)

(72) Inventor: Saeri Saito, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/058,287

(22) Filed: Mar. 2, 2016

(65) Prior Publication Data

US 2016/0174811 A1   Jun. 23, 2016

Related U.S. Application Data

(63) Continuation of application No. PCT/JP2015/058379, filed on Mar. 19, 2015.

(30) Foreign Application Priority Data

Jun. 23, 2014   (JP) .................................. 2014-128428

(51) Int. Cl.
*A61B 1/04* (2006.01)
*A61B 1/06* (2006.01)
(Continued)

(52) U.S. Cl.
CPC ...... *A61B 1/00009* (2013.01); *A61B 1/00011* (2013.01); *A61B 1/04* (2013.01);
(Continued)

(58) Field of Classification Search
CPC ... A61B 1/00009; A61B 1/00011; A61B 1/04; G02B 23/24; H04N 2005/2255; H04N 5/2253; H04N 5/2258; H04N 5/3415
See application file for complete search history.

(56) References Cited

U.S. PATENT DOCUMENTS 4,517,587 A * 5/1985 Aizawa .................... H04N 3/15
                                                        348/521
5,225,908 A * 7/1993 Lee ....................... H04N 1/2112
                                                        348/521
(Continued)

FOREIGN PATENT DOCUMENTS

CN       103260499 A     8/2013
JP       2002-165108 A   6/2002
(Continued)

OTHER PUBLICATIONS

International Search Report dated Jun. 16, 2015 issued in PCT/JP2015/058379.
(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An imaging device includes: first and second image sensors; a first communication controller configured to be connected to the first image sensor; a first clock generator that generates a first clock signal that is a reference for operation of the first communication controller; a second communication controller configured to be connected to the second image sensor; a second clock generator that generates a second clock signal that is a reference for operation of the second communication controller; a reference synchronization signal generator that generates a reference synchronization signal; and an imaging synchronization signal generator that generates an imaging synchronization signal which is a trigger for determining timings of imaging by the first and second image sensors, and outputs the imaging synchronization signal to the first and second communication controllers at a timing when a predetermined period of time has
(Continued)

elapsed from a reference timing based on the reference synchronization signal.

5 Claims, 8 Drawing Sheets

(51) Int. Cl.

| | | |
|---|---|---|
| *A61B 1/00* | (2006.01) | |
| *G02B 23/24* | (2006.01) | |
| *H04N 5/225* | (2006.01) | |
| *H04N 5/341* | (2011.01) | |
| *A61B 1/045* | (2006.01) | |
| *H04N 5/376* | (2011.01) | |
| *H04N 5/378* | (2011.01) | |

(52) U.S. Cl.
CPC ............. *A61B 1/045* (2013.01); *G02B 23/24* (2013.01); *G02B 23/2476* (2013.01); *H04N 5/2253* (2013.01); *H04N 5/2258* (2013.01); *H04N 5/3415* (2013.01); *H04N 5/378* (2013.01); *H04N 5/3765* (2013.01); *H04N 2005/2255* (2013.01)

(56) References Cited

U.S. PATENT DOCUMENTS

| | | | | |
|---|---|---|---|---|
| 8,401,090 | B2* | 3/2013 | Compton | ........... H04N 21/4305 |
| | | | | 348/500 |
| 8,823,789 | B2 | 9/2014 | Ono | |
| 2004/0183920 | A1 | 9/2004 | Tanimoto | |
| 2011/0267458 | A1* | 11/2011 | Kubo | .................. A61B 1/00009 |
| | | | | 348/135 |
| 2013/0010084 | A1* | 1/2013 | Hatano | ................... G03B 35/08 |
| | | | | 348/47 |
| 2013/0063659 | A1* | 3/2013 | Takahashi | .......... H04N 21/4307 |
| | | | | 348/521 |
| 2013/0093953 | A1* | 4/2013 | Miyashita | ............ H04N 5/3532 |
| | | | | 348/521 |
| 2013/0096376 | A1* | 4/2013 | Takei | ................. G02B 23/2461 |
| | | | | 600/103 |
| 2013/0208101 | A1* | 8/2013 | Ono | .................... A61B 1/00193 |
| | | | | 348/65 |
| 2014/0225998 | A1* | 8/2014 | Dai | ................... H01L 27/14601 |
| | | | | 348/65 |
| 2014/0371535 | A1* | 12/2014 | Seto | ..................... A61B 1/0661 |
| | | | | 600/160 |
| 2015/0035967 | A1* | 2/2015 | Wodnicki | ............... H04N 7/183 |
| | | | | 348/82 |

FOREIGN PATENT DOCUMENTS

| | | |
|---|---|---|
| JP | 2004-248003 A | 9/2004 |
| JP | 2005-303673 A | 10/2005 |
| JP | 2006-181021 A | 7/2006 |
| JP | 2014-107840 A | 6/2014 |
| WO | WO 2013/024788 A1 | 2/2013 |

OTHER PUBLICATIONS

Japanese Office Action dated Nov. 4, 2015 issued in JP 2015-539982.

Chinese Office Action dated Jan. 23, 2017 in Chinese Patent Application No. 201580001630.3.

* cited by examiner

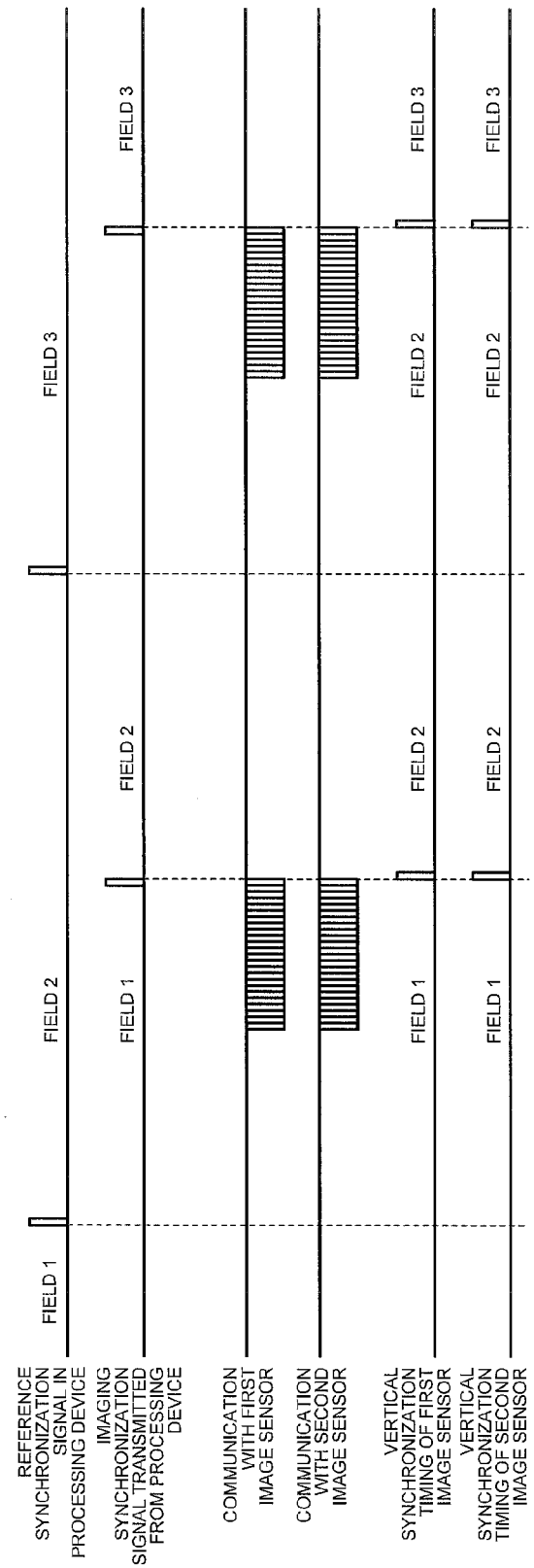

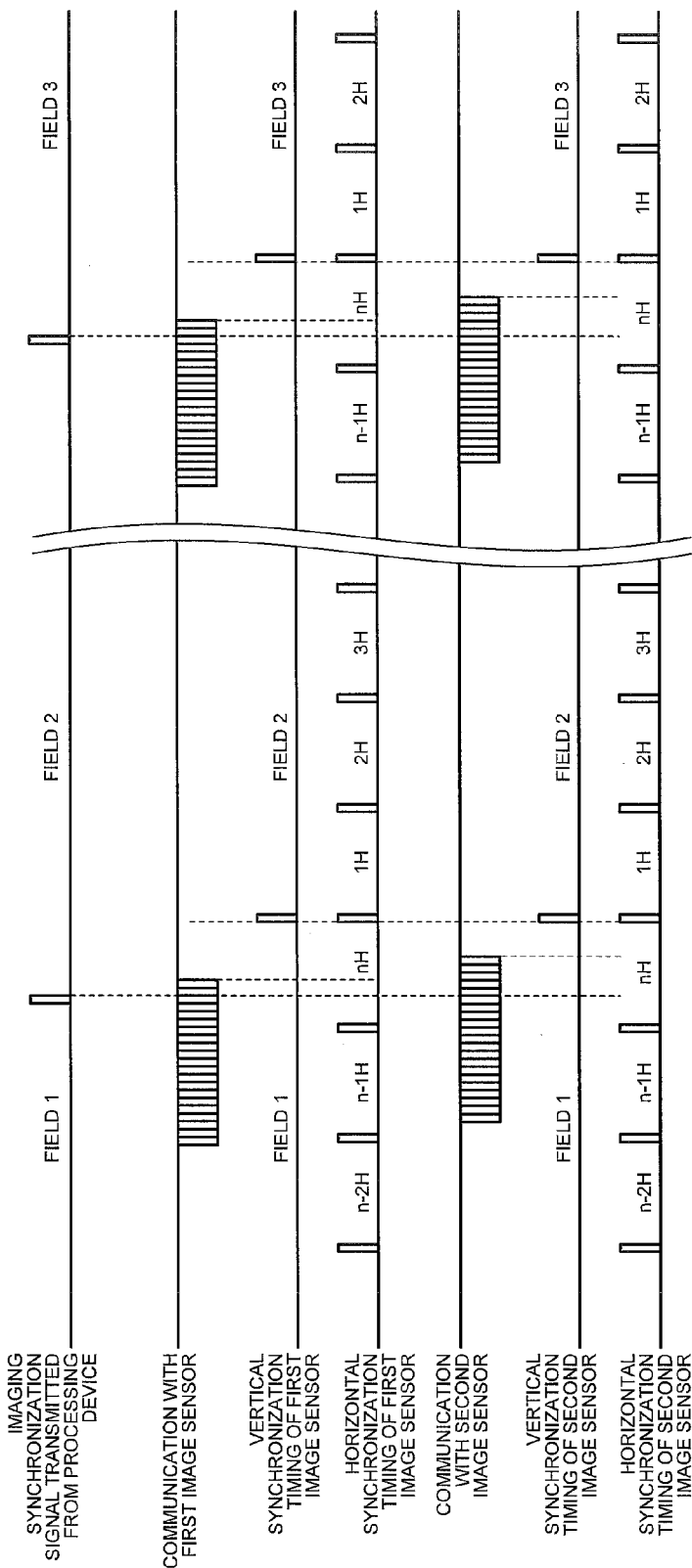

IMAGE DEVICE FOR SYNCHRONIZING TIMING OF IMAGING BY FIRST AND SECOND IMAGE SENSORS, AND ENDOSCOPIC DEVICE

CROSS-REFERENCE TO RELATED APPLICATIONS

This application is a continuation of PCT international application Ser. No. PCT/JP2015/058379 filed on Mar. 19, 2015 which designates the United States, incorporated herein by reference, and which claims the benefit of priority from Japanese Patent Application No. 2014-128428, filed on Jun. 23, 2014, incorporated herein by reference.

BACKGROUND

1. Technical Field

The disclosure relates to an imaging device including a plurality of image sensors, and to an endoscopic device.

2. Related Art

Endoscopic systems have been used to observe an organ of a subject such as a patient in the medical field. The endoscopic system includes: an endoscope that includes an insertion unit provided with an image sensor on its tip, having flexibility and an elongated shape, and configured to be inserted into a body cavity of the subject; and a processing device that is connected to the proximal end of the insertion unit through a cable, processes an in-vivo image in accordance with the imaging signals generated by the image sensor, and displays the in-vivo image, for example, on a display unit.

A technique in which an endoscopic system is provided with a plurality of image sensors including CMOS image sensors on a tip of an endoscope so as to generate a three-dimensional image or generate a clear two-dimensional image based on the images taken by the image sensors has been known (for example, Japanese Patent Application Laid-open No. 2006-181021). For example, the image sensors are connected to a processing device through dedicated lines (parallel bus) so as to transmit signals in Japanese Patent Application Laid-open No. 2006-181021. A timing generator generates a signal for driving the image sensors using a common clock, and this synchronizes the image sensors in Japanese Patent Application Laid-open No. 2006-181021.

SUMMARY

In some embodiments, an imaging device includes: first and second image sensors configured to receive light and to perform photoelectric conversion on the received light to generate electric signals; a first communication controller configured to be connected to the first image sensor to perform communication with the first image sensor and to control the communication to perform operating control on the first image sensor; a first clock generator configured to generate a first clock signal that is a reference for operation of the first communication controller; a second communication controller configured to be connected to the second image sensor to perform communication with the second image sensor and to control the communication to perform operating control on the second image sensor; a second clock generator configured to generate a second clock signal that is a reference for operation of the second communication controller; a reference synchronization signal generator configured to generate a reference synchronization signal; and an imaging synchronization signal generator configured to generate an imaging synchronization signal that is a trigger for determining timings of imaging by the first and second image sensors, and to output the imaging synchronization signal to the first and second communication controllers at a timing when a predetermined period of time has elapsed from a reference timing based on the reference synchronization signal. When the first and second communication controllers perform synchronization control communications for synchronizing the timings of imaging by the first and second image sensors, the first and second communication controllers are configured to determine the timings of imaging by the first and second image sensors using the imaging synchronization signal output from the imaging synchronization signal generator as a trigger.

In some embodiments, an endoscopic device includes: an insertion unit that has an elongated shape and is configured to be inserted into a living body; first and second image sensors configured to receive light and to perform photoelectric conversion on the received light to generate electric signals; a first communication controller configured to be connected to the first image sensor to perform communication with the first image sensor and to control the communication to perform operating control on the first image sensor; a first clock generator configured to generate a first clock signal that is a reference for operation of the first communication controller; a second communication controller configured to be connected to the second image sensor to perform communication with the second image sensor and to control the communication to perform operating control on the second image sensor; a second clock generator configured to generate a second clock signal that is a reference for operation of the second communication controller; a reference synchronization signal generator configured to generate a reference synchronization signal; and an imaging synchronization signal generator configured to generate an imaging synchronization signal that is a trigger for determining timings of imaging by the first and second image sensors, and to output the imaging synchronization signal to the first and second communication controllers at a timing when a predetermined period of time has elapsed from a reference timing based on the reference synchronization signal. When the first and second communication controllers perform synchronization control communications for synchronizing the timings of imaging by the first and second image sensors, the first and second communication controllers are configured to determine the timings of imaging by the first and second image sensors using the imaging synchronization signal output from the imaging synchronization signal generator as a trigger.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a timing chart of the control timing of the endoscopic system according to the first embodiment of the present invention;

FIG. 6 is a timing chart of the control timing of the endoscopic system according to the second embodiment of the present invention.

DETAILED DESCRIPTION

Modes for carrying out the present invention (hereinafter, referred to as "embodiment(s)") will be described below. A medical endoscopic system that takes an image of the inside of the body cavity of a subject such as a patient and displays the image will be described in the embodiments as an exemplary system including the imaging device and endoscopic device according to the present invention. The present invention is not limited to the embodiments. The same reference signs are used to designate the same elements throughout the drawings.

First Embodiment

Figure 1:
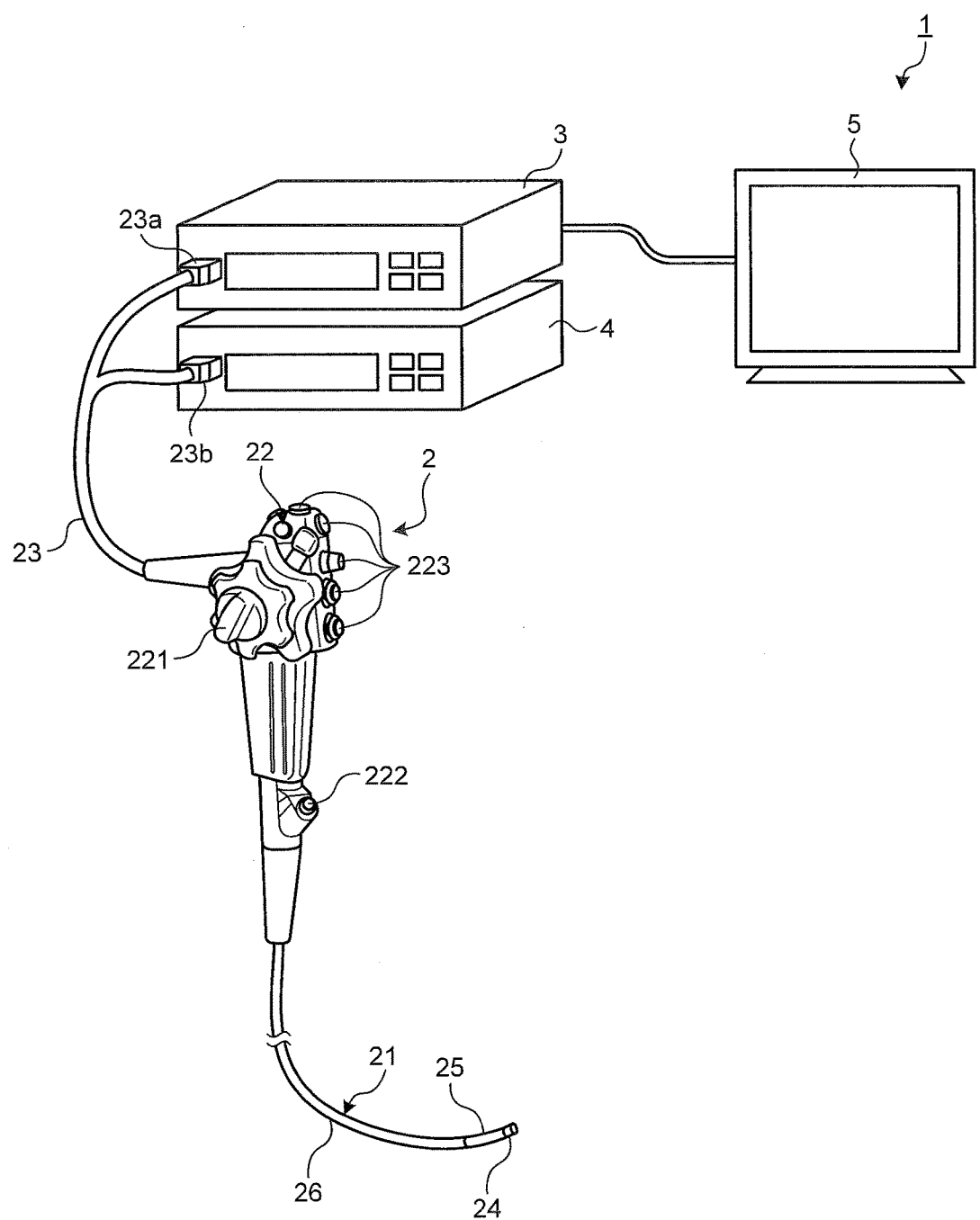
FIG. 1 is a schematic diagram of the configuration of an endoscopic system according to a first embodiment of the present invention.
Figure 2A:
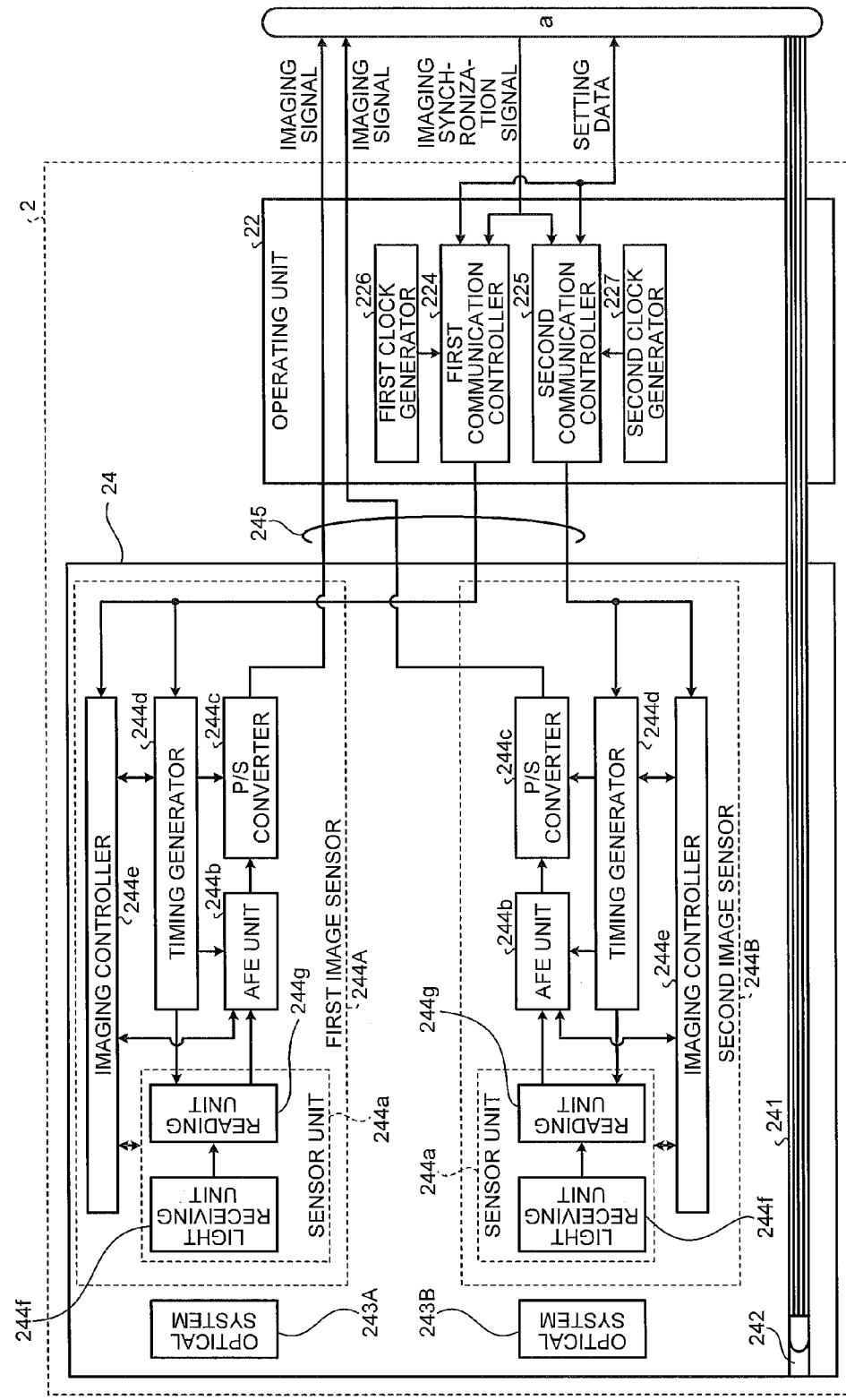
FIGS. 2A and 2B are schematic block diagrams of the configuration of the endoscopic system according to the first embodiment of the present invention.
Figure 2B:
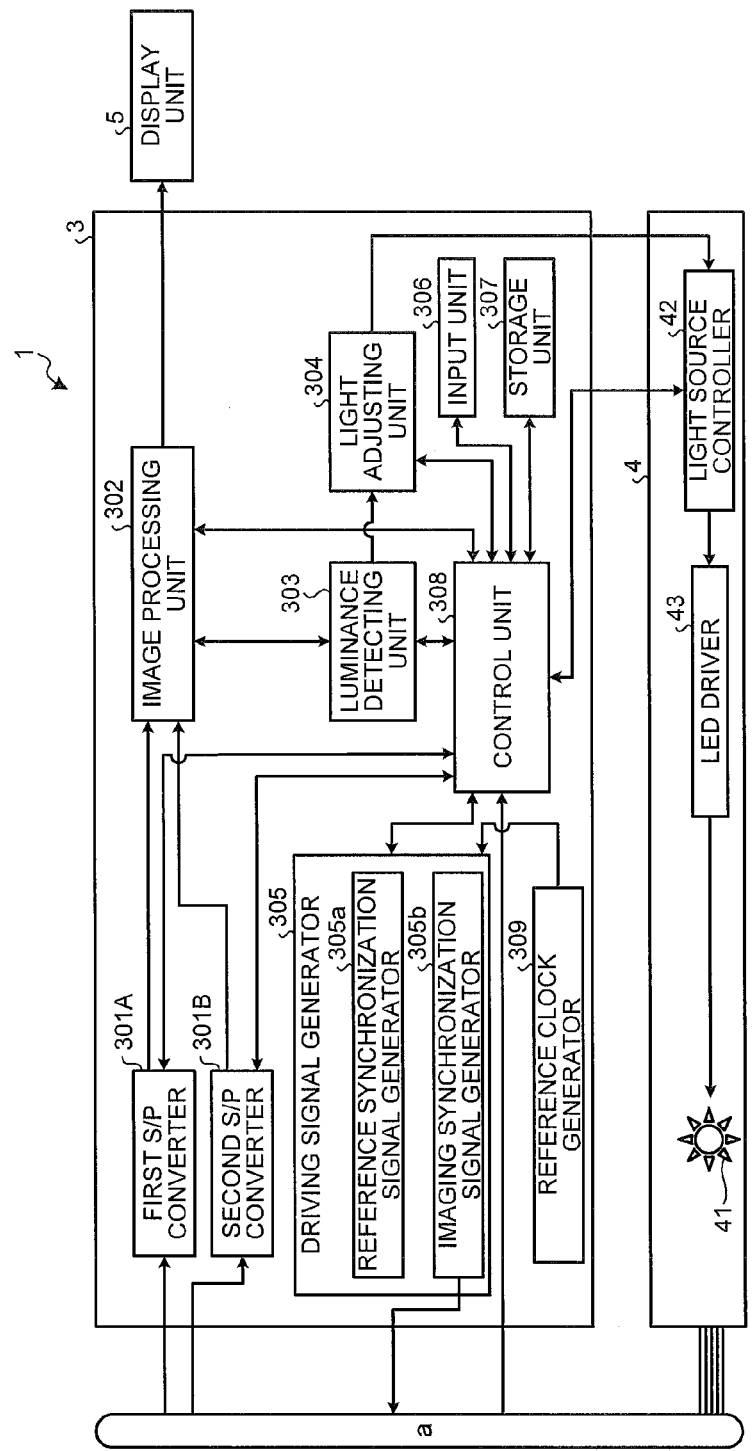

FIG. 1 is a schematic diagram of the configuration of an endoscopic system according to a first embodiment of the present invention. FIGS. 2A and 2B are schematic block diagrams of the configuration of the endoscopic system according to the first embodiment of the present invention.

An endoscopic system 1 illustrated in FIG. 1 and FIGS. 2A and 2B includes: an endoscope 2 whose tip is configured to be inserted into a body cavity of a subject to capture an in-vivo image of the subject; a processing device 3 that processes the in-vivo image taken with the endoscope 2 in a predetermined image process, and generally controls the operations of the whole endoscopic system 1; a light source device 4 that generates an illumination light to be emitted from the tip of the endoscope 2; and a display device 5 that displays the in-vivo image processed with the processing device 3.

The endoscope 2 includes: an insertion unit 21 that has flexibility and elongated shape; an operating unit 22 that is connected to the proximal end of the insertion unit 21 so as to receive the input of various operation signals; and a universal cord 23 that extends in a direction opposite to the direction in which the insertion unit 21 extends from the operating unit 22, includes connectors 23a and 23b connected to the processing device 3 and the light source device 4, respectively, and incorporates various cables therein.

The insertion unit 21 includes a tip portion 24 that incorporates an image sensor in which pixels, which generate signals by receiving light and performing photoelectric conversion on the received light, are two-dimensionally arranged; a curved portion 25 that is formed by a plurality of curved bridges and can curve freely; and a long flexible pipe portion 26 that is connected to the proximal end of the curved portion 25.

The tip portion 24 includes a light guide 241, an illumination lens 242, two optical systems (optical systems 243A and 243B), a first image sensor 244A, and a second image sensor 244B.

The light guide 241 is made, for example, of glass fiber and is a light guiding path for light emitted from the light source device 4. The illumination lens 242 is a lens that is provided on a tip of the light guide 241 and emits the illumination light.

The optical systems 243A and 243B are configured to collect light. Each of the optical systems 243A and 243B includes one or plurality of lenses. The optical systems 243A and 243B can have an optical zoom function to vary the angle of view or a focus function to vary the focal point.

Each of the first image sensor 244A and the second image sensor 244B includes: a sensor unit 244a that performs photoelectric conversion on the light collected by each of the optical systems 243A and 243B and generates an electric signal (hereinafter, referred to as an imaging signal); an analog front end unit 244b (hereinafter, referred to as an "AFE unit 244b") that removes noise from the imaging signal output from the sensor unit 244a and performs A/D conversion on the imaging signal; a P/S converter 244c that performs parallel-serial conversion on the imaging signal (a digital signal) output from the AFE unit 244b and transmits the converted imaging signal to the outside (the processing device 3); a timing generator 244d that generates the driving timing of the sensor unit 244a, and the pulses for various signal processes in the AFE unit 244b and P/S converter 244c; and an imaging controller 244e that controls the operation of the first image sensor 244A or the second image sensor 244B. Each of the first image sensor 244A and the second image sensor 244B is implemented with a Complementary Metal Oxide Semiconductor (CMOS) image sensor.

The sensor unit 244a includes a light receiving unit 244f and a reading unit 244g. In the light receiving unit 244f, a plurality of pixels each having a photodiode and a capacitor is arranged in a matrix form. The photodiode accumulates electric charge depending on the amount of light. The capacitor converts the electric charge transferred from the photodiode into a voltage level. Each of the pixels performs photoelectric conversion on the light from the optical system 243A or 243B to generate an electric signal. The reading unit 244g sequentially reads the electric signals generated by the pixels that are arbitrarily set as reading targets among the plurality of pixels in the light receiving unit 244f, and outputs the electric signals as imaging signals. A color filter is provided on a light-receiving surface of the light receiving unit 244f. The reading unit 244g sequentially reads, for each horizontal line, the electric signals generated by the plurality of pixels arranged in a matrix form.

The AFE unit 244b includes: a noise reduction circuit that reduces the noise contents included in the analog imaging signals, for example, using a Correlated Double Sampling method; an Automatic Gain Control (AGC) circuit that maintains the output at a constant level by adjusting the amplification factor (gain) of the imaging signal (the electric signal); and an A/D conversion circuit that performs A/D conversion on the imaging signal output through the AGC circuit.

The imaging controller 244e controls each of the operations of the first image sensor 244A or the second image sensor 244B in accordance with the control signal on the received setting data or the synchronization control. The imaging controller 244e, for example, outputs the reading signal to the reading unit 244g and controls the output of the electric signal output from each pixel by the pixel. The imaging controller 244e includes, for example, a Central Processing Unit (CPU) or a register that stores various programs.

The operating unit 22 is provided with: a curving knob 221 that curves the curved portion 25 up and down, and right and left; a treatment tool insertion unit 222 for inserting a treatment tool such as biopsy forceps, an electrical scalpel, or an inspection probe into the body cavity of the subject; and a plurality of switches 223 that are operation input units configured to input the instruction signals for the operations of peripheral devices such as an air feeding unit, a water feeding unit, and an image display control in addition to the processing device 3 and the light source device 4. The treatment tool inserted from the treatment tool insertion unit 222 extends outside from an opening portion (not illustrated) through a treatment tool channel (not illustrated) of the tip portion 24.

The operating unit 22 further includes a first communication controller 224, a second communication controller 225, a first clock generator 226, and a second clock generator 227. The first communication controller 224 controls the driving timing at which the first image sensor 244A is driven in accordance with the setting data received from the processing device 3 or the control signal on synchronization control. The second communication controller 225 controls the driving timing at which the second image sensor 244B is driven in accordance with the setting data received from the processing device 3 or the control signal on synchronization control. The first clock generator 226 generates a clock signal (a first clock signal) to drive the first communication controller 224. The second clock generator 227 generates a clock signal (a second clock signal) to drive the second communication controller 225. Note that the first clock generator 226 can be embedded in the first communication controller 224 and the second clock generator 227 can be embedded in the second communication controller 225. A microcomputer having a clock generating circuit is used for the first communication controller or the second communication controller, for example.

The universal cord 23 incorporates at least the light guide 241 and a cable assembly 245 having one or more signal lines. The cable assembly 245 includes a signal line to transmit and receive the setting data, and a signal line to transmit and receive an imaging signal.

The configuration of the processing device 3 will be described next. The processing device 3 includes a first S/P converter 301A, a second S/P converter 301B, an image processing unit 302, a luminance detecting unit 303, a light adjusting unit 304, a driving signal generator 305, an input unit 306, a storage unit 307, a control unit 308, and a reference clock generator 309 (a third clock generator).

The first S/P converter 301A and the second S/P converter 301B preform serial-parallel conversion on the imaging signals (digital signals) received from the tip portion 24 (the first image sensor 244A and the second image sensor 244B), respectively, and output the converted imaging signals to the image processing unit 302.

The image processing unit 302 generates image signals to be displayed with the display device 5 based on the imaging signals input from the first S/P converter 301A and the second S/P converter 301B. The image processing unit 302 generates image signals including an in-vivo image to be displayed by processing the imaging signals in an predetermined image process. The image process includes a synchronization process, an optical black subtraction process, a white balance adjusting process, a color matrix operation process, a gamma correction process, a color reproduction process, an edge enhancement process, a synthesizing process for synthesizing a plurality of image data items, and a format conversion process. The image processing unit 302 generates image signals including a three-dimensional image, or a two-dimensional image having a large number of pixels based on the imaging signals generated by the first image sensor 244A and the second image sensor 244B. The image processing unit 302 further outputs the imaging signals input from the first S/P converter 301A and the second S/P converter 301B to the control unit 308 or the luminance detecting unit 303.

The luminance detecting unit 303 detects the luminance level corresponding to each pixel from the image signals of RGB components output from the image processing unit 302. The luminance detecting unit 303 records the detected luminance level in an internal memory, and outputs the detected luminance level to the control unit 308. The luminance detecting unit 303 calculates a gain adjusting value and the amount of light irradiation based on the detected luminance level. The luminance detecting unit 303 outputs the calculated gain adjusting value to the image processing unit 302 while outputting the calculated amount of light irradiation to the light adjusting unit 304.

The light adjusting unit 304 sets the amount of light generated by the light source device 4 and the light emitting timing in accordance with the amount of light irradiation calculated by the luminance detecting unit 303 under the control by the control unit 308. Then, the light adjusting unit 304 transmits the control signals including the set conditions to the light source device 4.

The driving signal generator 305 generates a drive synchronization signal for driving the first image sensor 244A and the second image sensor 244B, and transmits the drive synchronization signal to the first communication controller 224 and the second communication controller 225.

The driving signal generator 305 includes a reference synchronization signal generator 305a, and an imaging synchronization signal generator 305b. The reference synchronization signal generator 305a generates synchronization signals based on the clock signal generated by the reference clock generator 309. The synchronization signals generated by the reference synchronization signal generator 305a include reference synchronization signals that are references for the operation of each unit in the processing device 3 and the operations of the endoscope 2 and the light source device 4.

The imaging synchronization signal generator 305b generates an imaging synchronization signal to drive the first image sensor 244A and the second image sensor 244B based on the clock signal generated by the reference clock generator 309, and outputs the imaging synchronization signal to the first communication controller 224 and the second communication controller 225. Specifically, the imaging synchronization signal generator 305b outputs an imaging synchronization signal. The imaging synchronization signal is a trigger for determining the imaging timing for the first image sensor 244A and the second image sensor 244B to start an imaging operation in response to the processing time of the first communication controller 224 and the second communication controller 225. The imaging timing is the starting timing at which an imaging operation starts. The imaging operation is for reading and obtaining the electric signals of a frame in an image.

The input unit 306 receives the input of the various signals such as an operation instruction signal that instructs the operation of the endoscopic system 1.

The storage unit 307 is implemented with a semiconductor memory such a flash memory or a Dynamic Random Access Memory (DRAM). The storage unit 307 stores various programs for operating the endoscopic system 1, and the data including various parameters necessary for the operation of the endoscopic system 1.

The control unit 308 includes a CPU. The control unit 308 controls the driving of each of the elements including the tip portion 24 and the light source device 4, and controls the input and output of information to and from each of the elements. The control unit 308 transmits the setting data for controlling the imaging process to the imaging controller 244e through a predetermined signal line in the cable assembly 245. The setting data includes the imaging rate (frame rate) of each of the first image sensor 244A and the second image sensor 244B, settings for an electronic shutter or gain, the instruction information for instructing the reading rate at which the pixel information is read from an arbitrary pixel in the sensor unit 244a, and the transmitting control information of the pixel information read by the AFE unit 244b.

The reference clock generator 309 generates a clock signal (a third clock) that is the reference for the operation of each element in the endoscopic system 1, and provides the generated clock signal to each element in the endoscopic system 1. In the first embodiment, a clock signal that the reference clock generator 309 generates is precise in comparison with the clock signals that the first clock generator 226 and the second clock generator 227 generate. Specifically, the oscillator of the reference clock generator 309 create a precise frequency in comparison with the frequencies created with the oscillators of the first clock generator 226 and the second clock generator 227.

The configuration of the light source device 4 will be described next. The light source device 4 includes a white light source 41, a light source controller 42, and a Light Emitting Diode (LED) driver 43.

The white light source 41 includes a white LED and generates a white illumination light under the control by the light source controller 42.

The light source controller 42 controls the amount of current to be supplied to the white light source 41 in accordance with the control signal transmitted from the light adjusting unit 304.

The LED driver 43 makes the white light source 41 generate the illumination light by supplying the current to the white light source 41 under the control by the light source controller 42. The light generated by the white light source 41 is emitted from the front end of the tip portion 24 through the light guide 241 to the outside.

Note that a special light source to generate an excitation light that excites a fluorescent material introduced in the subject can be provided in the light source device 4. The special light source generates, for example, an infrared light. The special light source can generate, as special light, light of any one of color components red, green, and blue at a wavelength band that is different from the wavelength band of the white luminance light and narrowed with a narrow band pass filter. The special light can be, for example, a Narrow Band Imaging (NBI) illumination light of two types of blue light and green light at narrowed bandwidths so that the special light can easily be absorbed in hemoglobin in the blood.

The display device 5 has a function to receive the in-vivo image generated by the processing device 3 through an image cable and displays the image. The display device 5 includes a display such as a liquid crystal display, or an organic Electro Luminescence (EL) display.

Note that the first image sensor 244A, the second image sensor 244B, the first communication controller 224, the second communication controller 225, the first clock generator 226, the second clock generator 227, the reference synchronization signal generator 305a, and the imaging synchronization signal generator 305b are used to constitute the imaging device (the endoscopic device) in the first embodiment.

Figure 4:
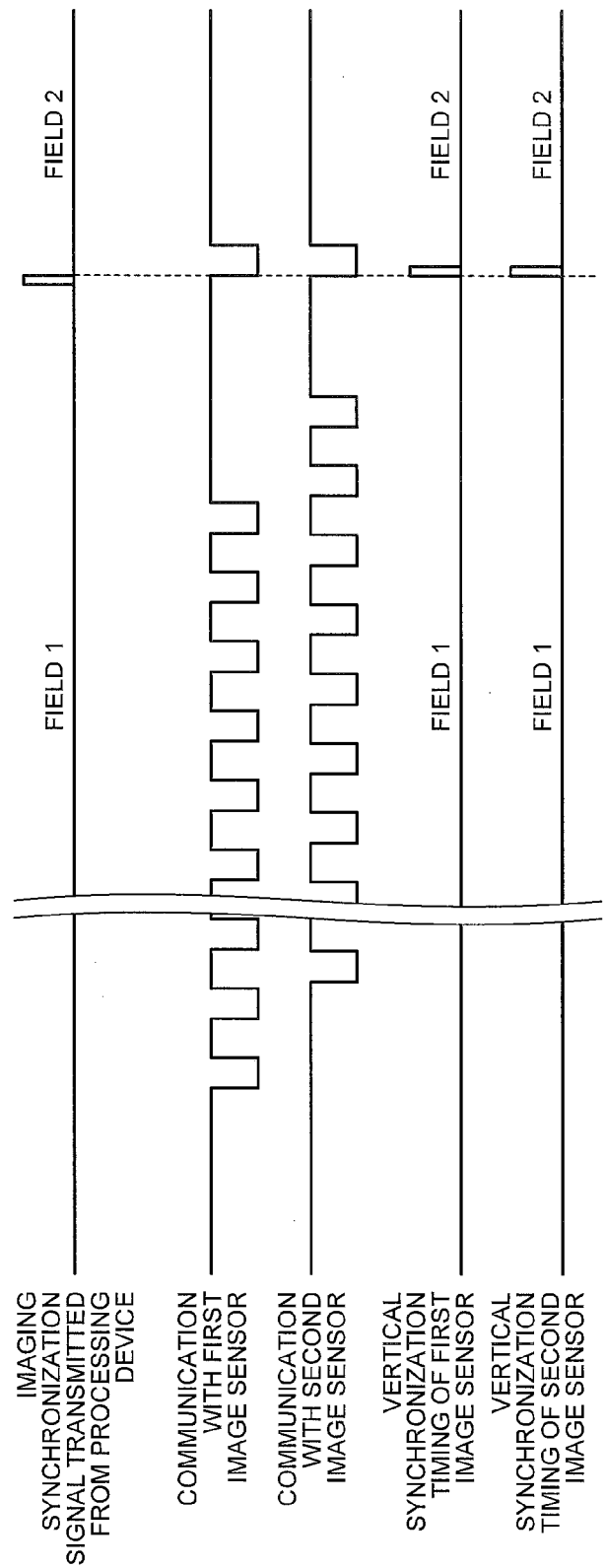
FIG. 4 is a timing chart of the control timing of the endoscopic system according to the first embodiment of the present invention, illustrating a part of FIG. 3 in more detail.

The synchronization control of the imaging timing in the endoscopic system 1 will be described next with reference to FIGS. 3 and 4. FIG. 3 is a timing chart of the control timing of the endoscopic system according to the first embodiment. FIG. 4 is a timing chart of the control timing of the endoscopic system according to the first embodiment, illustrating a part of FIG. 3 in more detail.

The first image sensor 244A and the second image sensor 244B alternately repeat the exposure on the light receiving unit 244f and the reading of an electric signal of a horizontal line with the reading unit 244g so as to obtain the imaging signals including the in-vivo image of the subject. The first image sensor 244A and the second image sensor 244B alternately read each of first to n-th horizontal lines (of a frame) at different points in time. In the first embodiment, a period required for the exposure process and reading process with the first image sensor 244A and the second image sensor 244B is referred to as a field. The reading process is for reading the electric signal generated by the exposure process. In other words, for example, an exposure process and a reading process for obtaining the electric signals (the imaging signals) of a frame included in an image are performed in a field.

The field is switched from a field 1 to a field 2 at an internal synchronization timing (a reference synchronization signal) in the processing device 3. The reference timing based on the synchronization timing (the reference synchronization signal) sometimes differs from a desired timing at which the image sensor starts the reading process. In light of the foregoing, the control unit 308 transmits the synchronization signal generated in the imaging synchronization signal generator 305b to the first communication controller 224 and the second communication controller 225.

The first communication controller 224 and the second communication controller 225 start a synchronization control communication, using the reference synchronization signal from the driving signal generator 305 as a trigger for the communication. The synchronization control communication is for synchronization control that determines an imaging timing (vertical synchronization timing) and includes the settings (register settings) for the operation conditions of the first image sensor 244A and the second image sensor 244B. At that time, the first communication controller 224 starts the synchronization control communication after counting a predetermined period of time from the synchronization timing based on the clock signal generated in the first clock generator 226. Meanwhile, the second communication controller 225 starts the synchronization control communication after counting a predetermined period of time from the synchronization timing based on the clock signal generated in the second clock generator 227. In the register settings, the control unit 308 transmits the setting data, for example, in a publicly known communication standard such as I²C or SPI so that various settings for each image sensor (for example, the settings for controlling the luminance of the electronic shutter, the designation of the device, and the designation of the address) are configured.

After that, the imaging synchronization signal generated by the imaging synchronization signal generator 305b is transmitted to the endoscope 2 (the first communication controller 224 and the second communication controller 225). The imaging synchronization signal transmitted from the imaging synchronization signal generator 305b is used as a trigger for the control to complete the synchronization control communication, and a signal for determining the last communication in the synchronization control communication by the first communication controller 224 and the second communication controller 225.

Specifically, the imaging synchronization signal generator 305b counts the elapsed period between the synchronization timing of the processing device 3 and the timing of the last communication in the synchronization control communication by the first communication controller 224, and the elapsed period between the synchronization timing of the processing device 3 and the timing of the last communication in the synchronization control communication by the second communication controller 225. Then, the imaging synchronization signal generator 305b outputs an imaging synchronization signal at a timing determined in accordance with the amount of the time lag between the two elapsed periods (the number of clocks) and the timing of completing the synchronization control communications. For example, each of the first communication controller 224 and the second communication controller 225 performs the last communication, using the reception of the imaging synchronization signal as a trigger. The imaging synchronization signal generator 305b outputs the imaging synchronization signal after counting a predetermined period of time from the reference timing based on the synchronization timing (the reference synchronization signal). The reference timing can be an arbitrary timing, for example, the timing at which the reference synchronization signal is output, or the timing at which the first communication controller 224 or the second communication controller 225 starts the synchronization control communication. Note that the imaging synchronization signal generator 305b can determine the number of clocks (the elapsed period) by counting the period elapsed in the synchronization control communication previously performed, or by counting the period elapsed in the communication performed when the endoscopic system 1 starts.

As illustrated in FIG. 4, the first communication controller 224 performs the synchronization control communication based on the synchronization timing of the processing device 3, and suspends the communication until just before the last communication in the synchronization control communication. The second communication controller 225 performs the synchronization control communication based on the timing counted with the clocks generated by the second clock generator 227, and suspends the communication until just before the last communication in the synchronization control communication. The frequency of the clock generated in first clock generator 226 slightly differs from the frequency of the clock generated in the second clock generator 227. In FIG. 4, there is a time lag in counting between the second communication controller 225 and the first communication controller 224 even if the first communication controller 224 and the second communication controller 225 start a communication at the same time. Thus, the second communication controller 225 performs the communication at a timing later than a timing in the first communication controller 224. The first communication controller 224 and the second communication controller 225 perform the last communication in the synchronization control communication, using the imaging synchronization signal from the imaging synchronization signal generator 305b as a trigger.

Specifically, when the signal is latched with the falling edge of the last clock in the communication, the first communication controller 224 generates a falling clock with the imaging synchronization signal from the imaging synchronization signal generator 305b as illustrated in FIG. 4. The second communication controller 225 generates a falling clock, using the imaging synchronization signal as a trigger. Generating the falling clocks determines the vertical synchronization timing (imaging timing) of the first image sensor 244A and the second image sensor 244B, and switches the field. When the field is switched, the reading unit 244g starts a reading process.

The first communication controller 224 and the second communication controller 225 performed the last communication in the synchronization control communication, using the imaging synchronization signal counted with the reference clock as a trigger as described above. Thus, the points in time of completing synchronization control communication of the first communication controller 224 and the second communication controller 225 are approximately identical. This can control the synchronization between the first communication controller 224 and the second communication controller 225 with a high degree of accuracy even if there is a time lag between the periods counted with the first communication controller 224 and the second communication controller 225. Note that the timing at which the imaging synchronization signal is input is shorter than the period between the start and completion of the synchronization control communication by the first communication controller 224 and the second communication controller 225. In other words, the imaging synchronization signal is preferably output after the communications start.

According to the first embodiment, the first communication controller 224 and the second communication controller 225 perform the last communication in the synchronization control communication, using the imaging synchronization signal as a trigger. This determines the vertical synchronization timing (the imaging timing) of each of the first image sensor 244A and the second image sensor 244B. This can synchronize a plurality of image sensors with a high degree of accuracy.

In the first embodiment, for example, the first communication controller 224 counts a predetermined period of time based on the clocks generated by the first clock generator 226 so that the first image sensor 244A starts the synchronization control communication. Note that, however, the first communication controller 224 can start the communication, for example, at the communication starting timing (not illustrated) transmitted from the control unit 308. This can control also the communication starting timing with a high degree of accuracy although increasing the number of control lines.

In the first embodiment, the first communication controller 224 and the second communication controller 225 perform a synchronization control communication in every field. However, the first communication controller 224 and the second communication controller 225 can perform the communication every several fields or in predetermined fields.

In the first embodiment, the field is switched at the falling of the last pulse. However, the field can be switched after several clocks are counted from the falling of the last pulse.

In the first embodiment, the imaging synchronization signal is the trigger for the last communication. However, a falling clock can be generated just after the imaging synchronization signal is received, or the falling clock can be generated after several clocks are counted. The timing of the last communication can be controlled in any way as long as the reception of the imaging synchronization signal is used as the trigger.

In the first embodiment, the processing device 3 is provided with the imaging synchronization signal generator 305b. However, a counter can be provided in the endoscope 2, for example, in the connector 23a. In such a case, a clock generator corresponding to the reference clock generator 309 is preferably provided in the endoscope 2.

Second Embodiment

Figure 5A:
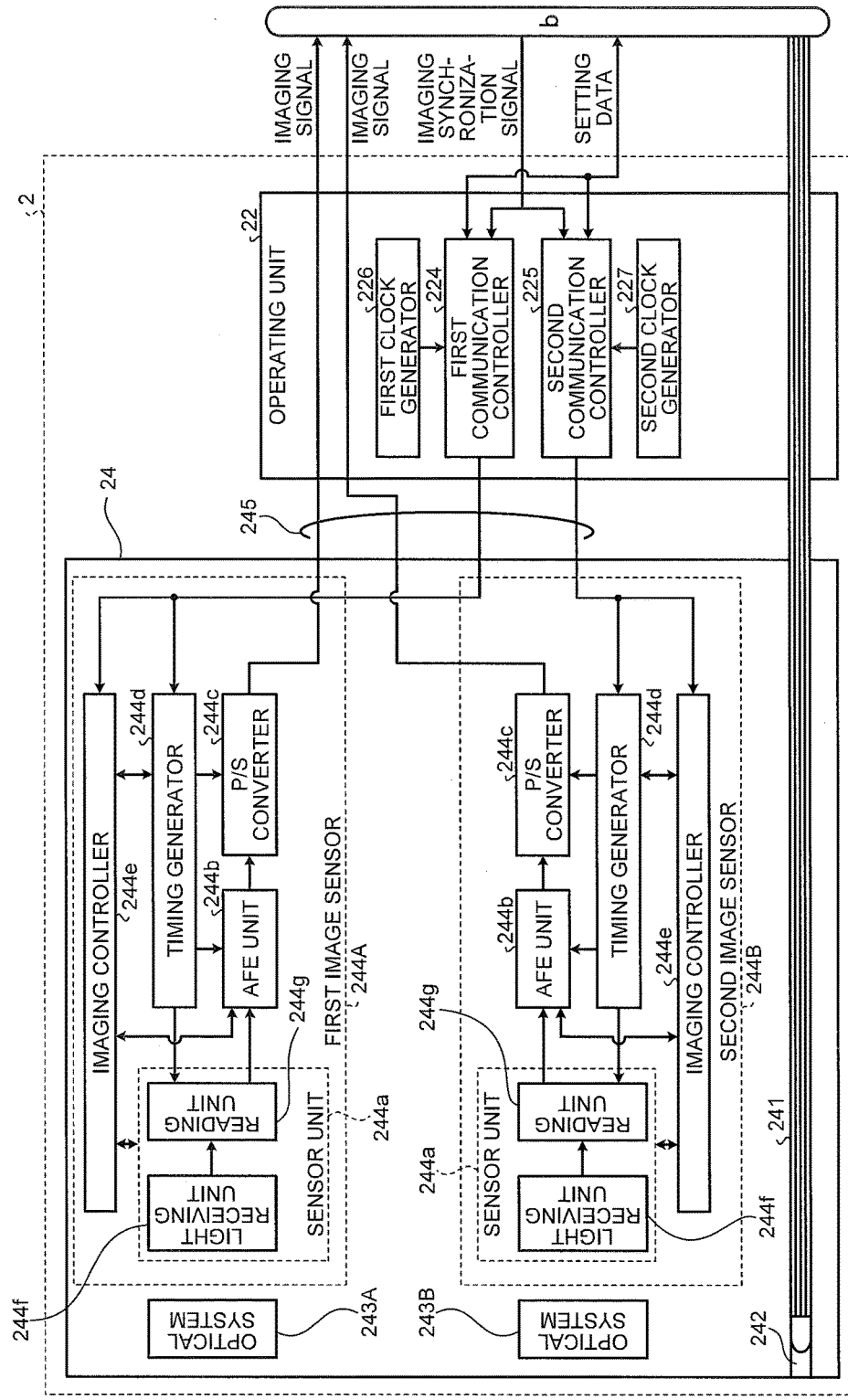
FIGS. 5A and 5B are schematic block diagrams of the configuration of an endoscopic system according to a second embodiment of the present invention.
Figure 5B:
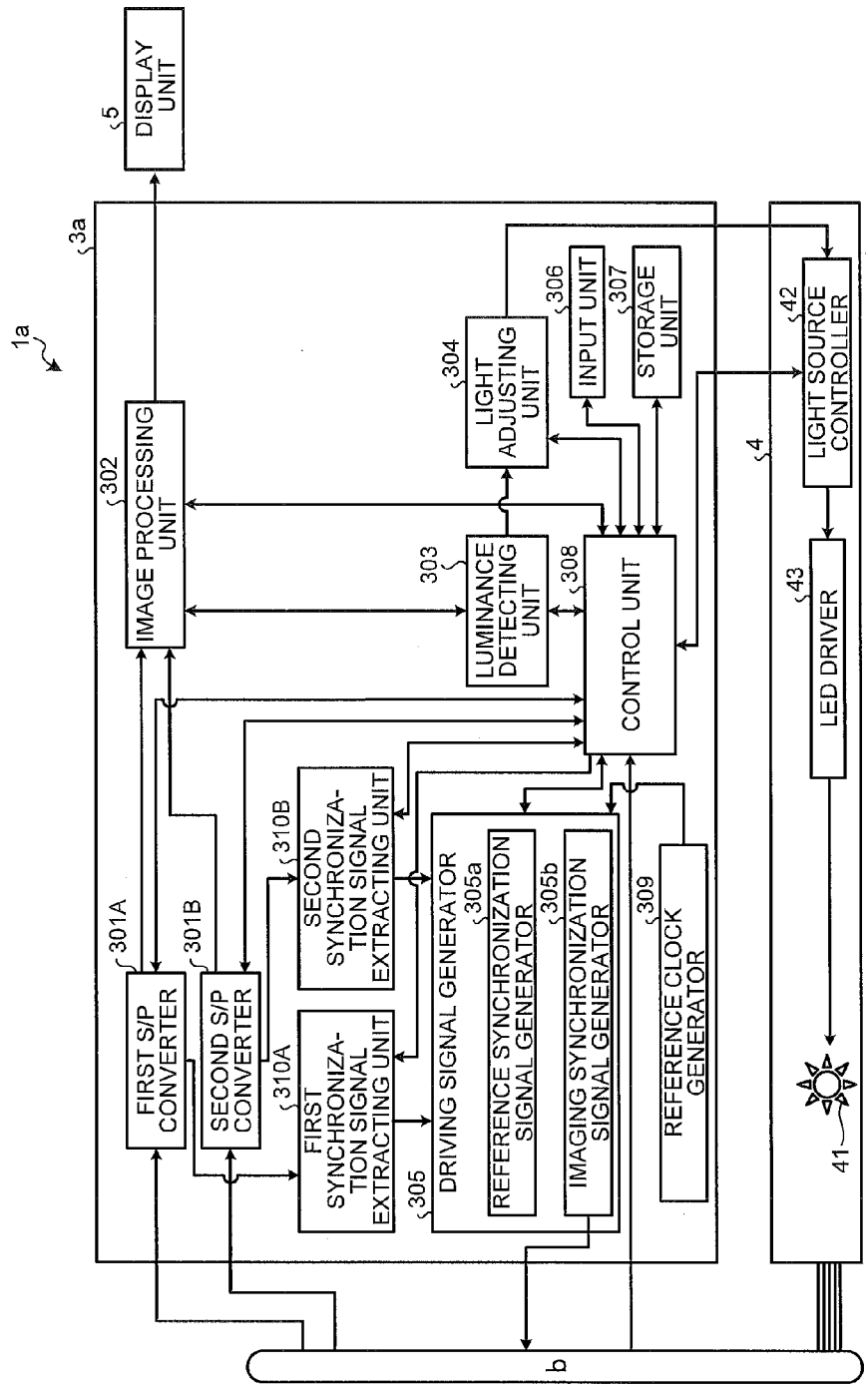

The second embodiment of the present invention will be described next. FIGS. 5A and 5B are schematic block diagrams of the configuration of an endoscopic system according to the second embodiment. The same elements as those in the above-described embodiment will be denoted by the same reference signs. In the second embodiment, a horizontal synchronization signal is extracted from the obtained imaging signals. The vertical synchronization timing is determined in accordance with the horizontal synchronization timing of a first image sensor 244A and a second image sensor 244B. Then, the field is switched.

An endoscopic system 1a according to the second embodiment includes an endoscope 2, a light source device 4, a display device 5, and a processing device 3a. The processing device 3a includes a first synchronization signal extracting unit 310A and a second synchronization signal extracting unit 310B in addition to the elements of the processing device 3. Note that the vertical synchronization timing of the first image sensor 244A and the second image sensor 244B is controlled by the horizontal synchronization timing in the second embodiment. Specifically, the register settings for each image sensor are configured. After the register settings is completed, a synchronization signal is generated in each image sensor based on the first horizontal synchronization timing. Each image sensor is driven in accordance with the generated synchronization signal. When the register settings are completed at different points in time, for example, when the first image sensor 244A completes the setting before the horizontal synchronization signal and the second image sensor 244B completes the setting after the horizontal synchronization signal, this generates a difference in timing of driving each of the image sensors by one horizontal synchronization period. The first image sensor 244A, the second image sensor 244B, a first communication controller 224, a second communication controller 225, a first clock generator 226, a second clock generator 227, a reference synchronization signal generator 305a, an imaging synchronization signal generator 305b, and the synchronization signal extracting unit (the first synchronization signal extracting unit 310A and the second synchronization signal extracting unit 310B) are used to constitute an imaging device in the second embodiment.

First, the first synchronization signal extracting unit 310A and the second synchronization signal extracting unit 310B obtain the imaging signals generated in the endoscope 2 through a first S/P converter 301A and a second S/P converter 301B, respectively. The first synchronization signal extracting unit 310A and the second synchronization signal extracting unit 310B separate the imaging signals into the image signals and the synchronization signals, and extract the horizontal synchronization signal from the separated signals.

The imaging synchronization signal generator 305b generates a horizontal synchronization signal in accordance with an interval between adjacent pulses in the horizontal synchronization signal extracted with each of the first synchronization signal extracting unit 310A and the second synchronization signal extracting unit 310B. Specifically, the imaging synchronization signal generator 305b generates an imaging synchronization signal. The imaging synchronization signal is output such that the timings of completing the communications of the first communication controller 224 and the second communication controller 225 are located at the same interval between the pulses. The imaging synchronization signal according to the second embodiment is the trigger for the control of the completion of the synchronization control communication. Specifically, when the imaging synchronization signal is received, the reception is used as the trigger for the last communication.

FIG. 6 is a timing chart of the control timing for controlling the endoscopic system according to the second embodiment. The first communication controller 224 and the second communication controller 225 start a synchronization control communication based on the clock that each of the first communication controller 224 and the second communication controller 225 counts, or start a synchronization control communication based on the synchronization timing of the processing device 3, similarly to the first embodiment.

When a synchronization signal is output from the imaging synchronization signal generator 305b in the synchronization control communication, the first communication controller 224 and the second communication controller 225 use the imaging synchronization signal as a trigger, and perform the synchronization control communication, for example, while suspending the synchronization control communication for a period of several clocks. Specifically, the first communication controller 224 and the second communication controller 225 delay the timing of completing communication by suspending the communication for a period of a set number of clocks until the first communication controller 224 and the second communication controller 225 perform the last communication in response to an imaging synchronization signal from the imaging synchronization signal generator 305b, as illustrated in FIG. 6. Note that the first communication controller 224 and the second communication controller 225 that suspend the communication just before the last communication in a synchronization control communication can perform the last communication and complete the communication, using the imaging synchronization signal as a trigger. This makes it possible to adjust the timings of completing the communications of the first image sensor 244A and the second image sensor 244B such that the timings are located in the same interval between the pulses of the horizontal synchronization signal (for example, at an interval nH in FIG. 6) and do not overlap with (do not match) the horizontal synchronization pulses. Thus, the horizontal synchronization timings for determining the vertical synchronization timings between the first image sensor 244A and the second image sensor 244B are matched. When the horizontal synchronization timings are matched, the vertical synchronization timings of the first image sensor 244A and the second image sensor 244B are also matched. The field can be switched with the corresponding vertical synchronization timing. After the field is switched, the reading unit 244g starts a reading process.

When the vertical synchronization timing of the first image sensor 244A and the vertical synchronization timing of the second image sensor 244B are controlled by the horizontal synchronization timing, the first communication controller 224 and the second communication controller 225 adjust the timing of completing the synchronization control, using the imaging synchronization signal as a trigger. It is therefore possible to control the synchronization between the first communication controller 224 and the second communication controller 225 with a high degree of accuracy even if there is a difference in counts between the first communication controller 224 and the second communication controller 225.

According to the second embodiment, the first communication controller 224 and the second communication controller 225 adjust the completion of the synchronization control by counting a predetermined number of clocks, using the imaging synchronization signal as a trigger. This leads to the matching between the horizontal synchronization timings and to the matching between the vertical synchronization timings. It is therefore possible to synchronize a plurality of image sensors with a high degree of accuracy.

In the second embodiment, the processing device 3 includes the imaging synchronization signal generator 305b, the first synchronization signal extracting unit 310A and the second synchronization signal extracting unit 310B. However, the counter and the synchronization signal extracting units can be provided in the endoscope 2, for example, in the connector 23a. In such a case, a clock generator corresponding to the reference clock generator 309 is preferably provided in the endoscope 2. The first synchronization signal extracting unit 310A and the second synchronization signal extracting unit 310B obtain the imaging signals from the AFE unit 244b or the P/S converter 244c, and extract the horizontal synchronization signals.

In the second embodiment, the completion of the synchronization signals may occur at different points in time as long as the timings of completing the synchronization control of the first communication controller 224 and the second communication controller 225 are located in the same interval between the pulses in the horizontal synchronization signal.

In the first and second embodiments, the vertical synchronization timing is determined with the timing at which the control communication is completed (or the horizontal synchronization timing just after the completion). Any data item in the control communication can be set as the timing data for determining the vertical synchronization timing instead of the timing at which the control communication is completed. In such a case, the imaging synchronization signal is transmitted so that the setting data is set at the timing (for example, at an interval between the horizontal synchronization pulses).

Note that, a rotation filter can be arranged on the light path on which the white light source 41 emits a white light in the first and second embodiments. The rotation filter includes a plurality of filters to make only light at predetermined wavelength bands in the white light penetrate by rotating the filters. The provided rotation filter makes the light having wavelength bands of the red light (R), green light (G), and blue light (B) sequentially penetrate so that the light are emitted. This can sequentially emit the red light (R illumination), green light (G illumination), and blue light (B illumination) at narrowed bandwidths in the white light that the white light source 41 emits (W illumination) to the endoscope 2 (in a frame sequential method). In the emission, performing the imaging control as described above can reduce the color deviation between the images.

In the first and second embodiments, the reference synchronization signal (the synchronization timing) for causing the first image sensor 244A and the second image sensor 244B to start the imaging operation is generated based on the clock signal generated by the reference clock generator 309. However, the reference synchronization signal can be generated based on the clock signal generated by the first clock generator 226, the second clock generator 227, or an external clock generator.

The synchronization between the two image sensors is controlled in the first and second embodiments. However, the imaging process can also be controlled when three or more image sensors are provided.

According to some embodiments, it is possible to synchronize a plurality of image sensors with a high degree of accuracy.

As described above, the imaging device and the endoscopic device according to some embodiments are useful for synchronizing a plurality of image sensors with a high degree of accuracy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
   first and second image sensors configured to receive light and to perform photoelectric conversion on the received light to generate electric signals;
   a first communication controller configured to be connected to the first image sensor to perform communication with the first image sensor and to control the communication to perform operating control on the first image sensor;
   a first clock generator configured to generate a first clock signal that is a reference for operation of the first communication controller;
   a second communication controller configured to be connected to the second image sensor to perform communication with the second image sensor and to control the communication to perform operating control on the second image sensor;
   a second clock generator configured to generate a second clock signal that is a reference for operation of the second communication controller;
   a reference synchronization signal generator configured to generate a reference synchronization signal; and
   an imaging synchronization signal generator configured to:
   generate an imaging synchronization signal; and
   output the imaging synchronization signal to the first and second communication controllers at a timing when a predetermined period of time has elapsed from a reference timing based on the reference synchronization signal,
   wherein the first and second communication controllers are configured to determine the timings of imaging by the first and second image sensors using the imaging synchronization signal output from the imaging synchronization signal generator as a trigger to perform synchronization control communications for synchronizing timings of imaging by the first and second image sensors.

2. The imaging device according to claim 1, further comprising a third clock generator configured to generate a third clock signal with higher precision of frequency than the first and second clock signals,
   wherein the reference synchronization signal generator is configured to generate the reference synchronization signal based on the third clock signal.

3. The imaging device according to claim 1, further comprising a synchronization signal extracting unit configured to extract a horizontal synchronization signal from the electric signals generated by the first and second image sensors, wherein the imaging synchronization signal generator is configured to generate the imaging synchronization signal such that timings of completing the synchronization control communications between the first and second image sensors and the first and second communication controllers are located in a same interval between horizontal synchronization pulses and do not overlap with the horizontal synchronization pulses.

4. The imaging device according to claim 1, wherein a timing of inputting the imaging synchronization signal is in a period of time between when the first and second communication controllers start the synchronization control communications and when the first and second communication controllers complete the synchronization control communications.

5. An endoscopic device comprising:
   an insertion unit that has an elongated shape and is configured to be inserted into a living body;
   first and second image sensors configured to receive light and to perform photoelectric conversion on the received light to generate electric signals;
   a first communication controller configured to be connected to the first image sensor to perform communication with the first image sensor and to control the communication to perform operating control on the first image sensor;
   a first clock generator configured to generate a first clock signal that is a reference for operation of the first communication controller;
   a second communication controller configured to be connected to the second image sensor to perform communication with the second image sensor and to control the communication to perform operating control on the second image sensor;
   a second clock generator configured to generate a second clock signal that is a reference for operation of the second communication controller;
   a reference synchronization signal generator configured to generate a reference synchronization signal; and
   an imaging synchronization signal generator configured to:
      generate an imaging synchronization signal; and
      output the imaging synchronization signal to the first and second communication controllers at a timing when a predetermined period of time has elapsed from a reference timing based on the reference synchronization signal,
   wherein the first and second communication controllers are configured to determine the timings of imaging by the first and second image sensors using the imaging synchronization signal output from the imaging synchronization signal generator as a trigger to perform synchronization control communications for synchronizing timings of imaging by the first and second image sensors.

* * * * *